United States Patent
Schmidt et al.

(10) Patent No.: US 9,030,551 B2
(45) Date of Patent: May 12, 2015

(54) AMBIENT REFLECTIVITY ABSORPTION SYSTEM FOR IDENTIFYING PRECIOUS OR SEMI-PRECIOUS MATERIALS AND ASSOCIATED METHODS

(75) Inventors: Dorn Schmidt, Park City, UT (US); Brad Wilson, Park City, UT (US)

(73) Assignee: Discovery Metals, LLC, Park City, UT (US)

( * ) Notice: Subject to any disclaimer, the term of this patent is extended or adjusted under 35 U.S.C. 154(b) by 538 days.

(21) Appl. No.: 13/479,934

(22) Filed: May 24, 2012

(65) Prior Publication Data
US 2013/0135461 A1    May 30, 2013

Related U.S. Application Data

(60) Provisional application No. 61/489,574, filed on May 24, 2011.

(51) Int. Cl.
| | |
|---|---|
| H04N 7/18 | (2006.01) |
| G01N 21/55 | (2014.01) |
| G01N 21/31 | (2006.01) |
| G01N 21/87 | (2006.01) |

(52) U.S. Cl.
CPC ............... *G01N 21/55* (2013.01); *G01N 21/314* (2013.01); *G01N 21/3151* (2013.01); *G01N 21/87* (2013.01); *G01N 2021/3155* (2013.01); *G01N 2021/3177* (2013.01); *G01N 2021/3181* (2013.01); *G01N 2201/0616* (2013.01)

(58) Field of Classification Search
CPC ....... G01N 21/55; G01N 21/87; G01N 21/33; G01N 21/39; G01N 21/314; G01N 21/3151; G01N 2021/3155; G01N 2021/3177

USPC ................................... 348/135; 356/445, 446
See application file for complete search history.

(56) References Cited

U.S. PATENT DOCUMENTS

| | | | | |
|---|---|---|---|---|
| 4,278,353 | A | * | 7/1981 | Ostermayer, Jr. ............. 356/416 |
| 4,900,147 | A | * | 2/1990 | Bowley et al. .................. 356/30 |

(Continued)

OTHER PUBLICATIONS

Lindfors et al; Detection and Spectroscopy of Gold Nanoparticles Using Supercontinuum White Light Confocal Nicroscopy; Physical Review Letters; Jul. 16, 2004; pp. 1-4; vol. 93, No. 3.

(Continued)

*Primary Examiner* — Sath V Perungavoor
*Assistant Examiner* — Nathnael Aynalem
(74) *Attorney, Agent, or Firm* — Thorpe North & Western, LLP (57) ABSTRACT

A reflectivity absorption system for identifying a target precious or semi-precious material can include a detector, a filter system, and an output display. The detector system is capable of detecting a reflected electromagnetic radiation at a primary wavelength and a secondary wavelength. The reflected electromagnetic radiation can be produced from sunlight or other light source. The primary wavelength corresponds to an upper reflectivity of the target material while the secondary wavelength corresponds to a lower reflectivity of the target material. Reflectivity is a function of wavelength such that identifiable variations in wavelength can be observed for certain materials over specific wavelength ranges which are then compared to a known standard reflectivity response for the indicated wavelengths. These systems can be used in portable, handheld, or stationary configurations and can identify exposed target materials in real-time.

24 Claims, 3 Drawing Sheets

(56) References Cited

U.S. PATENT DOCUMENTS

| | | |
|---|---|---|
| 5,195,626 A | 3/1993 | Le Hong et al. |
| 5,307,272 A | 4/1994 | Butlerl et al. |
| 5,696,490 A | 12/1997 | Maloney |
| 5,717,216 A * | 2/1998 | McCoy et al. ............ 250/372 |
| 6,147,350 A | 11/2000 | Beercroft et al. |
| 6,254,831 B1 * | 7/2001 | Barnard et al. ........... 422/82.08 |
| 6,509,968 B1 | 1/2003 | Woskov et al. |
| 6,645,772 B1 | 11/2003 | Kirby et al. |
| 6,917,433 B2 | 7/2005 | Levy et al. |
| 6,989,277 B2 | 1/2006 | Yang et al. |
| 7,477,309 B2 | 1/2009 | Cuccias |
| 7,545,140 B2 | 6/2009 | Humphreys et al. |
| 7,652,477 B2 | 1/2010 | Candy |
| 7,656,153 B2 | 2/2010 | Westersten |
| 7,679,063 B2 * | 3/2010 | Hoffman et al. ............ 250/375 |
| 7,701,204 B2 | 4/2010 | Westersten |
| 7,701,337 B2 | 4/2010 | Westersten |
| 7,791,337 B2 | 9/2010 | Simon |
| 7,816,920 B2 | 10/2010 | Qin et al. |
| 7,820,967 B2 | 10/2010 | DeMarco et al. |
| 2003/0059103 A1 | 3/2003 | Shiomi et al. |
| 2005/0117145 A1 * | 6/2005 | Altman et al. ............... 356/30 |
| 2007/0291157 A1 | 12/2007 | Ding et al. |
| 2009/0130771 A1 | 5/2009 | Davies et al. |
| 2013/0063717 A1 * | 3/2013 | Kawasaki et al. ............. 356/72 |

OTHER PUBLICATIONS

Nikitin et al; Photometric Method of Determining Gold Film Thickness of Nuclear Radiation Silicon Detectors; Izmeritel 'naya Tekhnika; Feb. 1987; pp. 52-53; issue No. 2.
Henry et al; Spectral Reflectance Curves to Distinguish Soybean from Commohn Cocklebur (Xanthium strumarium) and Sicklepod (Cassia obtusifolia) Grown with Varying Soil Moisture; Weed Science; 2004; pp. 788-796; vol. 52.
Shiraishi et al; Optical Properties of Au-Pt and Au-Pt-In Alloys; Gold Bulletin; 2001; pp. 129-133; vol. 34, No. 4.
Infrared Security Cameras and Infrared Camera Systems; http://www.surveilance-spy-cameras.com/day-night.htm; as accessed Oct. 29, 2010; 1 page.
Sony XC-EI301/3" B/W Analog Near Infrared Camera EIA; http://www.google.com/products/catalog?q=infrared+camera&r . . . ; as accessed Oct. 29, 2010; pp. 1-2.
Pyrite Mineral Data; http://webmineral.com/data/Pyrite.shtml; as accessed on Oct. 13, 2010; pp. 1-6.
Implementing Infrared Object Detection; http://www.seattlerobotics.org/guide/infrared.html; as accessed on Oct. 28, 2010, pp. 1-6.
U.S. Appl. No. 13/292,860, filed Nov. 9, 2011, Criz Bilbao.

* cited by examiner

AMBIENT REFLECTIVITY ABSORPTION SYSTEM FOR IDENTIFYING PRECIOUS OR SEMI-PRECIOUS MATERIALS AND ASSOCIATED METHODS

RELATED APPLICATIONS

This application claims the benefit of U.S. Provisional Application No. 61/489,574, filed May 24, 2011, which is incorporated herein by reference.

BACKGROUND

Precious metals have a multitude of uses which range from catalysis and conductors, to drug delivery vehicles and coinage. Identifying locations of precious metals in mines and surface deposits has long been a challenge. Current methods involve visual inspection, panning, sifting, assaying, and the like. Often these methods can be time consuming and may be inaccurate. For example, mining operations in vertical wellbores and horizontal drilling systems routinely collect samples from locations as formation rock is removed. Samples from removed material are typically taken to a testing site for assaying. This can often involve hours or more of delay before determining whether precious metals have been located. In some drilling operations further drilling can damage precious metal recovery options such that delays in assaying result in delays in operation. Further, precious metal detection also involves various surface scanning technologies which range from spurious to respectable technologies. However, each system has drawbacks ranging from poor sensitivity to poor accuracy.

SUMMARY

A reflectivity absorption system for identifying a target precious or semi-precious material can include a detector, a filter system, and an output display. The detector system is capable of detecting a reflected electromagnetic radiation at a primary wavelength and a secondary wavelength. The reflected electromagnetic radiation derives from reflection of electromagnetic radiation from a sample surface. The primary wavelength corresponds to an upper reflectivity of the target material. The secondary wavelength corresponds to a lower reflectivity of the target material. Additional wavelengths are possible in order to provide third, fourth or a larger number of reference points for correlation which a known standard. Reflectivity is a function of wavelength, although certain materials such as many precious and semi-precious materials have marked variation in reflectivity over selected wavelength ranges.

As a consequence, the filter system can be connected to the detector and configured to filter the reflected electromagnetic radiation into an upper spectral region and a lower spectral region. More specifically, the upper spectral region can encompass the primary wavelength and exclude the secondary wavelength. Further, the lower spectral region can encompass the secondary wavelength and exclude the primary wavelength. In this manner, substantial variations in reflectivity can be correlated with certain materials.

An output signal can be generated using the upper and lower spectral regions. The output display can be configured to register the output signal in a viewable format. In certain embodiments, the output signal can be spatially differentiable on the basis of different responses coming from different regions of the area scanned. This can allow for production of a video output display in which identified correlations can be highlighted with respect to locations. The output signal can be used directly or indirectly to correlate the output signal with a known standard for particular precious and semi-precious materials. These systems can be used in portable, handheld, or stationary configurations. Advantageously, these reflectivity absorption systems can identify exposed target materials in real-time.

A corresponding method of identifying a precious or semi-precious target material can also be provided which is based on reflectivity as utilized in the above-described system. The method can include collecting a reflected electromagnetic radiation from a sample surface. The reflected electromagnetic radiation includes a primary wavelength corresponding to an upper reflectivity of the target material and a secondary wavelength corresponding to a lower reflectivity of the target material. Conveniently, the incident electromagnetic radiation can be provided by artificial or natural sources for reflection to the detector. Thus, broadband or narrowband artificial lights can be used, although sunlight can also provide a suitable and ubiquitous light source.

The reflected electromagnetic radiation can be filtered into an upper spectral region and a lower spectral region. Additional optional filtering can be used to provide additional regions to improve signal accuracy. As with the system, the upper spectral region can encompass the primary wavelength and exclude the secondary wavelength, while the lower spectral region can encompass the secondary wavelength and exclude the primary wavelength. An output signal can be registered, the output signal being formed using the upper and lower spectral regions. Once the step of registering is accomplished, the sample surface can be identified as the target material by comparing the reflectivity response or output signal with a known standard.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

DEFINITIONS

In describing and claiming the present invention, the following terminology will be used.

The singular forms "a," "an," and "the" include plural referents unless the context clearly dictates otherwise. Thus, for example, reference to "a filter" includes reference to one or more of such devices and reference to "registering" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, "reflectivity" and "reflectance" are interchangeably used and refer to the percentage of incident radiation which is reflected from a sample surface.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Reflectivity Absorption Systems

Figure 1:
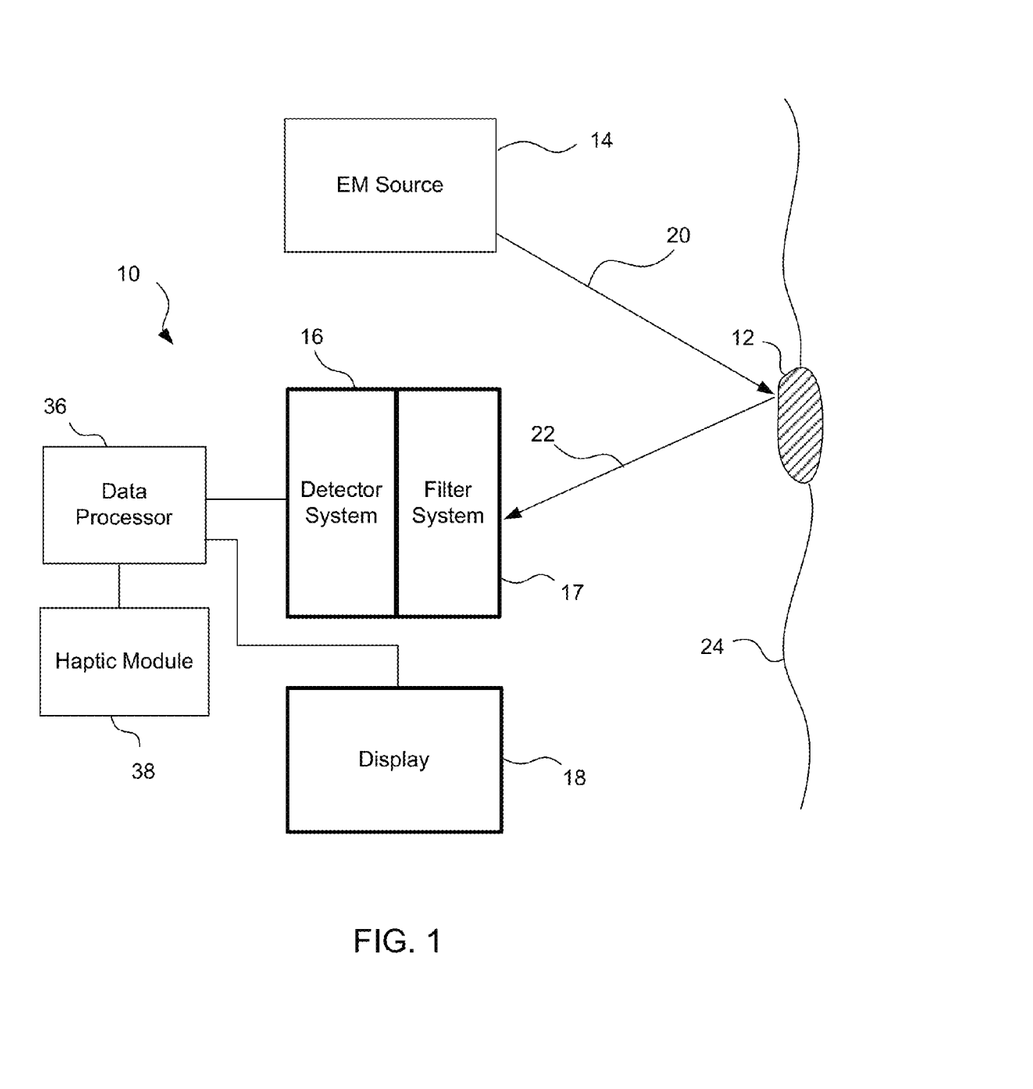
FIG. 1 is a schematic of a reflectivity absorption system in accordance with one embodiment.

Referring to FIG. 1, a reflectivity absorption system 10 for identifying a target material 12 can include an electromagnetic (EM) source 14, a detector system 16, a filter system 17, and an output display 18. The electromagnetic source can be a source which produces radiation at suitable wavelengths. Specifically, the EM source can emit incident electromagnetic radiation 20 which produces or strengthens a reflected electromagnetic radiation 22 from reflection of the incident electromagnetic radiation 20 from a sample surface 24. The reflected electromagnetic radiation can include, among other wavelengths, a primary wavelength and a secondary wavelength. The primary wavelength corresponds to an upper reflectivity of the target material 12. The secondary wavelength corresponds to a lower reflectivity of the target material 12.

The EM source 14 can be a suitable emitter which produces radiation which can be reflected from the sample surface 24 of a target material. Non-limiting examples of suitable emitters can include sunlight, fluorescent lights, light emitting diodes (LEDs), incandescent light sources, lasers, or the like. The fluorescent lights which lack a phosphorescent coating or have reduced amounts of such coating sufficient to increase emissions at shorter wavelengths (e.g. below about 300 nm for some materials). Sunlight can provide a simple and abundant source of broadband light which includes both the primary and secondary wavelengths. The EM source can often be a single source, although optionally can be provided using multiple sources simultaneously or successively staged. The emitter can be chosen to emit radiation at a specific wavelength or plurality of wavelengths (e.g. two, three, and up to narrow or full spectrum broadband).

The detector system 16 can be capable of detecting the reflected electromagnetic radiation at both the primary wavelength and the secondary wavelength. The detector can also be configured to detect reflected electromagnetic radiation at additional wavelength ranges. The detector system 16 can be provided as part of the system 10 in order to receive reflected radiation 22 from the sample surface 24.

The incident electromagnetic radiation 20 produced from the EM source 14 reflects from a sample surface 24 with a fraction of the incident radiation being reflected. The portion of radiation reflected is the reflected electromagnetic radiation 22. The fraction of radiation which is reflected at a given range of wavelengths determines the reflectivity for that range of wavelengths. Depending on the sample surface properties, the reflectivity varies accordingly.

The reflected radiation can be detected using a suitable detector system 16 which is sensitive to the primary wavelength, and other applicable wavelength ranges. Specifically, most detector systems can detect or collect radiation at a predetermined range of wavelengths (i.e. a characteristic bandwidth). The detector can be any suitable detector such as, but not limited to, a Charge-Coupled Device (CCD), IR diode, multiple LED photo diode light sensors, and the like. In embodiments involving CCDs, the CCD selected may be a back illuminated CCD and/or a delta doped CCD to extend sensitivity into the ultraviolet region.

In one aspect, the detector can be configured to detect and collect visible and infrared radiation. In another aspect, the detector system can be configured to detect and collect infrared and ultraviolet radiation. This can be useful in producing a visual video display. In one optional aspect, the detector can be one or more LED photo diode light sensors. Such LED photo diode light sensors may include infrared (IR) diodes for larger wavelengths and LEDs that emit at the desired wavelength, for shorter wavelengths in the visible and ultraviolet, but that have been reverse biased to function as photodiodes. In embodiments where such photodiodes are employed, the photodiodes themselves may also act as filters over the range of wavelengths for which they are sensitive.

The primary wavelength can be chosen to correspond to an upper reflectivity of the target material. Specifically, precious or semi-precious materials uniquely exhibit a spectral reflectivity curve where a dramatic increase in reflectivity occurs in the infrared range and especially in the near infrared range. Therefore, the primary wavelength can be chosen to correspond to a relatively high reflectivity for precious and semi-precious materials.

Figure 2A:
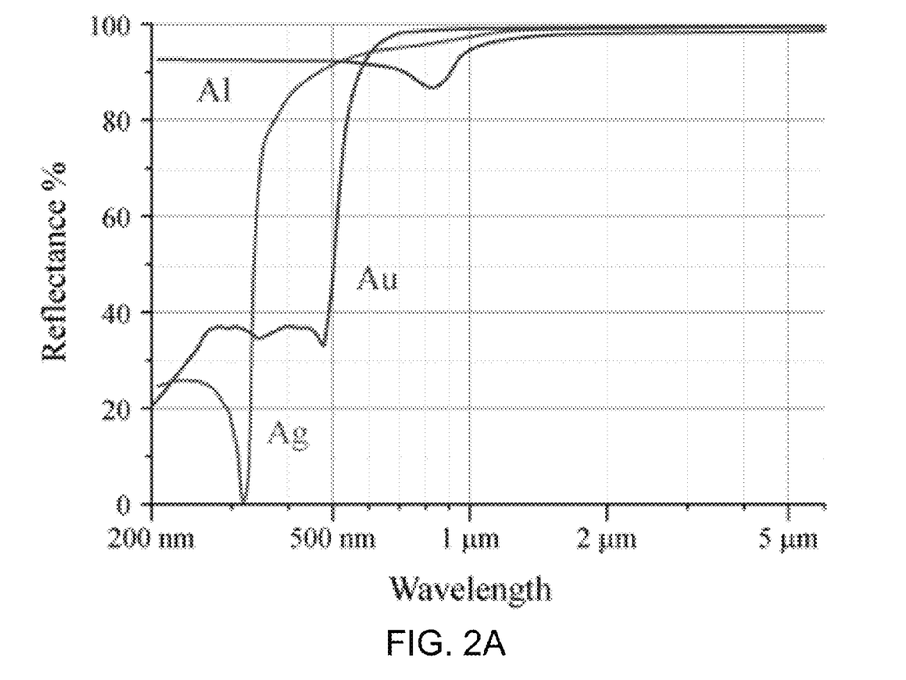
FIG. 2A is a graph of reflectivity versus wavelength for gold, silver and aluminum.
Figure 2B:
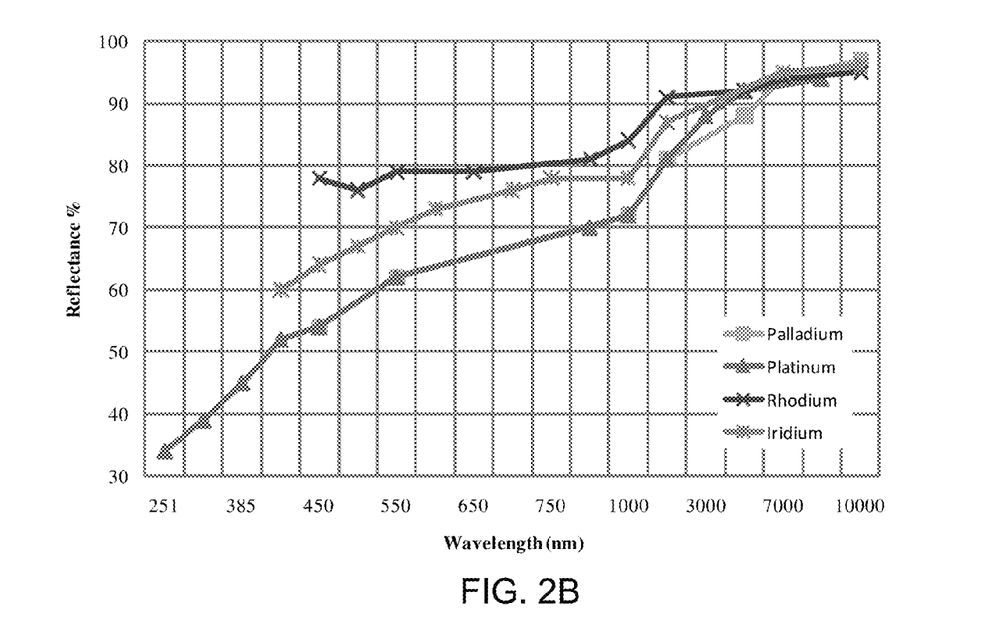
FIG. 2B is a graph of reflectivity versus wavelength for platinum, palladium, rhodium and iridium.

Associating the primary wavelength with longer wavelengths is further supported by the fact that the reflectivity within a region of longer visible light wavelengths to infrared wavelengths for precious metals is substantially higher than most other materials. Referring to FIG. 2A, a steep increase in reflectivity is observed for gold (Au) at 480 nm to about 600 nm. From about 600 nm to about 1 µm, the reflectivity for gold is higher than most materials. This reflectivity of gold in this region is commonly about 60% greater than the reflectivity of other materials. Thus, an emitter primarily emitting wavelengths from about 650 nm to about 1 µm can be particularly desirable for gold. In one embodiment, emitters are chosen to emit primarily wavelengths around 850 nm, although other values can be used (e.g. 730 nm, 880 nm and 940 nm). Similarly, the target precious metal can be silver. In such case, it is noted that reflectivity of silver begins a dramatic increase around 310 nm up to about 500 nm. Thus, the primary wavelength for silver may be from about 500 nm to about 1 µm, although slightly lower or higher wavelengths can also be suitable if distinguishable from surrounding materials. Similar reflectivity curves are evident for other precious metals such as palladium, platinum, rhodium and iridium as shown in FIG. 2B.

The secondary wavelength may be chosen to correspond to wavelengths from a region of relatively low reflectivity. Many target materials have relatively low reflectivity at shorter wavelengths. For example, as discussed and as depicted in FIG. 2A, there are dramatic changes in the reflectivity of gold and silver between the wavelengths of 480 nm to 600 nm and 310 nm to about 500 nm for gold and silver respectively. In light of these reflectivity characteristics for gold and silver, the secondary wavelength can be chosen to focus on a short wavelength such as, without limitation, 450 nm for gold and 300 nm for silver. Optimally, for silver, a value of 350 nm can be chosen to take advantage of even more pronounced change in reflectivity occasioned by the dip in reflectivity at wavelengths surrounding this mark.

By choosing ranges of wavelengths associated with both strong and weak response, a target, such as a target material may be detected on the basis of the change in responses characteristic of the target with respect to the various wavelengths. For example, with respect to gold and silver, a change in reflectivity of greater than 50% over the relevant wavelengths is indicative of the presence of these precious metals. Additional ranges of wavelengths can provide additional information to facilitate detection and increase degree of confidence in successful detection of the target material.

Returning to the primary wavelength, the upper reflectivity can be sufficiently high, in and of itself, to distinguish reflected radiation signals for surrounding materials from those of the target precious or semi-precious material. In one aspect, the upper reflectivity for target materials is greater than 95%. However, the absolute magnitude of the reflectivity may be less important than the relative difference between competing signals. Thus, it can be suitable to choose a primary wavelength which allows for a reflectivity difference sufficient to visually or computationally distinguish the target material. As a general guideline, this can be from about 5% to about 50%, depending on the particular test surface and conditions.

In addition, the response for the secondary wavelength can be used as an additional point of reference. In many situations, the characteristic reflectivity of the target will be lower than that of surrounding materials. This is the situation in FIG. 2A, where the response for aluminum is high relative to those of gold and silver. This is important because there is much less difference between the reflectivity of the three materials at longer wavelengths where the primary wavelength would be located. As a result it would be more difficult to detect gold and silver in an aluminum rich environment using solely the primary wavelength. By collecting data for two or more ranges of wavelengths, background materials that may have similar reflectivity to a target at one range of wavelengths can be distinguished by additional information from second or additional wavelength.

In one specific aspect, the lower reflectivity of the target material can be at least 20% lower than the upper reflectivity. The tolerance of this difference can be optionally adjustable to allow for increased or decreased sensitivity. For example, surfaces having a high amount of aluminum may need a higher tolerance (i.e. lower reflectivity difference) in order to trigger recognition of potential target precious or semi-precious material presence.

The EM source intensity may be varied and will affect the illumination range and increase reflected signal intensity. An increase in total emitter intensity can be achieved using higher power emitters and/or multiple emitters. For example, emitter power can typically range from about 1 µW to about 200 mW per emitter, although other powers can be used. Illumination range can vary from about 4 feet up to 500 feet or more, although there is no technical range limitation and is only limited by the emitter output power and resolution of the detector. Incident radiation can be introduced at an angle and detected at an angle based on characteristic angular dependence of reflectivity. However, the present embodiments are well suited for environments characterized by diffuse reflection.

Referring again to FIG. 1, the detector system 16 can be a single common detector to receive reflected radiation at both the primary and secondary wavelength. Optionally, a dedicated detector can be provided for each wavelength to form the detector system. This can allow for optimization of signals and/or modularization of the device.

The detector system 16 can have a filter system 17 operatively associated therewith. Typically, the reflected electromagnetic radiation 22 will include a broadband radiation such that isolation of wavelengths and/or bandwidths are desirable in order to highlight variations in reflectivity associated with desired target materials (e.g. precious and semi-precious materials). Accordingly, the filter system 17 can be configured to filter the reflected electromagnetic radiation 22 into an upper spectral region and a lower spectral region. The upper spectral region encompasses the primary wavelength and excludes the secondary wavelength. Conversely, the lower spectral region encompasses the secondary wavelength and excludes the primary wavelength. Additional wavelengths can be isolated and collected by additional filters in some embodiments.

The filter system 17 can typically be oriented to filter the reflected electromagnetic radiation prior to detection by the detector system. The filter system can include one or more filters which form the spectral regions. The filters may be optical filters that can be band-pass filters (i.e. isolate a specific band of wavelengths) or low/high pass filters (i.e. isolate an upper or lower wavelength range). For example, a first band-pass filter can form the lower spectral region and a second band-pass filter can form the upper spectral region. In this case, each of the lower and upper spectral regions are distinctly defined ranges (e.g. 300-600 nm, 800 nm-1 µm, etc). Alternatively, the filter system can include a low-pass filter to form the upper spectral region and a high-pass filter to form the lower spectral region. In this case, each of the upper and lower spectral regions are open ended (i.e. less than 600 nm, greater than 1 µm, etc).

In embodiments involving CCD, individual filters can be applied to individual sensor elements to generate a filter layer over a sensor layer comprising a CCD. The filter layer can comprise different filters configured to pass different wavelengths and block different wavelengths with respect to other filters. These filters may be arranged in a pattern across the CCD so that different elements are sensitive to different wavelengths. These filters can be high pass, low pass, or band pass filters.

The filter pattern can be made up of filters sensitive to only two different groups of wavelengths or filters sensitive to many different wavelength groups. In embodiments with filters sensitive to only two different groups of wavelengths, filters sensitive to the first group of wavelengths can be configured to pass the primary wavelength(s) and filters sensitive the second group of wavelengths can be configured to pass the secondary wavelengths. Regardless of the number of kinds of filters, each filter from the group of different types may be arranged adjacent to the others in a pattern that is repeated across the CCD.

In one aspect, the filter system 17 can be oriented subsequent to detection. For example, the filter system can be a filter processor or software which processes signals collected by the detector. Such a filter system can isolate the upper and lower spectral regions as outlined above using software (or hardcoded chips).

The system can optionally further include a processor 36 coupled with one or more units of memory. The processor 36 may also be used to improve accuracy and sensitivity of received data. Furthermore, a polarizer and/or polarization filter can be used to polarize incoming radiation and/or incident radiation. The system can optionally include a profile module coupled to the processor, which can adjust filtered bandwidths and corresponding spectral regions, sensitivity, and/or signal output based on a desired target precious or semi-precious material, as discussed below. For example, optimal wavelengths and signal processing for gold detection will be slightly different from those for silver, although common settings may be used for both. As such, memory in the profile module can store and apply different settings depending on the target material. The profile module can be connected to at least one of the detector 16 and the display 18. Optionally, the profile module can act as a central processor which analyzes and prepares raw data for display at the output display 18.

As one option, the system can be modular to allow for variation in the filter system. Thus, instead of having a dedicated internal profile module, the filters can be user replaceable. For example, the filter system can be present in a filter housing which is user detachable from the system. A suitable releasable connector for power and optional data communication can be provided. The filter housing can also include a suitable release mechanism which removably secures the emitter housing to a primary housing of the system. Non-limiting examples of release mechanisms can include latches, threads, snaps, detent, recessed lug and nut, and the like.

In certain embodiments, one or more tunable optical filters can be incorporated to selectively isolate the desired wavelength or range of wavelengths for further processing. Examples of such tunable filters may include, without limitation, liquid crystal tunable filters and tunable Fabry-Pérot interferometers, but other technologies may be applied. A tunable optical filter can be tuned to collect data for multiple ranges of frequencies very quickly. Tunable optical filters have the advantage of being able to take data from the exact location without concern for alteration in a line of sight, which may occur during filter changes.

The system can further include a processor 36 coupled to one or more memory units for comparing the reflected electromagnetic radiation with a standard. The standard can define a response at one or more ranges of wavelengths for one or more target precious metals. This processor can be common with the optional profile module or present as a separate unit.

The processor 36 can be used to compare reflectivities with one another, and with a set threshold and/or with stored values for specific target materials. More specifically, the data processor 36 can be used to transform the upper spectral region and the lower spectral region into the output signal. The output signal can comprise numerical values for isolated sub-signals such as reflectivity in the upper and lower spectral regions and/or the difference between the two regions. Isolated sub-signals need not only be defined for distinct ranges of frequencies, but may also be provided for different spatial regions. In such scenarios, responses are differentiated and resolved corresponding to distinct responses from distinct spatial regions being scanned. Embodiments with CCDs lend themselves particularly to spatially distinct responses, as discussed in more detail below with respect to the display.

This type of output signal, and portions thereof, can then be correlated by a user against a known standard. Alternatively, the data processor can correlate the upper and lower spectral regions with stored values for known precious and/or semi-precious materials. The data processor can then produce a positive or negative signal based on these correlations. In this way, the output signal can be readily distinguished by a user. Optionally, the filter processor can be an integrated portion of the data processor or a dedicated processor.

In embodiments with tunable optical filters, such filters may be coupled with the processor 36 and memory to receive tuning commands. The tuning commands can be configured to tune the optical filter to collect different ranges of wavelengths. These ranges of wavelengths may be stored in memory so that they are accessible to the processor. Furthermore, these wavelengths may correspond to signature regions of a reflectivity response for a given precious or semi-precious material. In such embodiments, the processor generates tuning commands with information stored in memory for a specific precious metal for which the system has been set for detection.

The output display 18 is configured to register an output signal in a viewable format. The output signal can be formed using the upper and lower spectral regions and information obtained from the reflected and filtered radiation. The output display 18 is provided to communicate to a user information recorded about the surface properties. The output display 18 can optionally be integral with the detector system in a common housing. This configuration can be useful as a mobile and/or handheld device which is fully stand alone. Alternatively, the output display can be remotely connected to the detector via an output connection. For example, the output connection can be wired or wireless using any available and functional protocol. Non-limiting examples of such wireless communication can include Bluetooth, infrared, 802.11 standards, radio frequency (RF), laser light, optical, and the like. Wired connections can include, but are not limited to, optical fibers, copper wire, and the like.

The output display 18 can be configured for a variety of formats. For example, in many applications, the output display can be a video display. A video display offers convenient visual recognition by a user and correlation to a specific location to tag the target material. In some applications, non-video output can be provided in the form of a single output such as magnitude of signal or the like. In one option, the output display can be a numerical readout or bar graph. In another aspect, the output display may be an analog display (e.g. needle).

The specific implementation of the system can vary widely depending on the intended use and desired results. For example, an individual person seeking precious or semi-precious materials for weekend recreation may have different expected operational parameters than would be expected by an industrial assayer. Thus, in one alternative, the system can be a fully integrated mobile system which is handheld. The output display can be wirelessly connected or wired, or merely a computer monitor which displays information retrieved from the detector system and processor unit. As such, depending on the connection choice, the output display can be real-time or delayed.

In embodiments involving a CCD, spacing in the array of the CCD, corresponding to the spacing of the pixels in the display, may be used to locate responses in two dimensional space. In such embodiments, the lens channeling electromagnetic radiation to the CCD may be pointed like a camera. Groups of one or more sensor elements in the CCD correspond to pixels on the video display, with each group corresponding to a particular pixel. For this reason it can be desirable to group sensors with different filters adjacent to one another in a group and repeat the pattern across the CCD so that groups can correspond to different response locations in the scanned area. Therefore, responses from each group of sensor elements in the system can be depicted on the video display relative to the spatial location of other responses within the spatial confines of the two dimensions provided by the video display.

By increasing the resolution of the CCD, the area, at a given distance, for which a response can be registered in a pixel of the video display becomes smaller and smaller. As this area becomes smaller, smaller deposits of a target material may be detected in a given pixel. Alternatively, since the physical area that can be reported by a single pixel increases with distance, acceptable distances for detection are increased with increasing CCD resolution. If the distance is too great, however, the response registered in each pixel will include responses from materials other than the target material in sufficient quantities to obscure the signal from the precious metal.

In such embodiments, the response registered in each pixel of the display can correspond to the response at a single range of wavelengths or it may correspond to some resultant combination of multiple ranges of wavelengths, such as the difference between the responses from the primary wavelength and the secondary wavelength. In certain embodiments, certain pixels may be dedicated to certain ranges of wavelengths while other pixels may be dedicated to other ranges of wavelengths.

In some embodiments, a pixel on the display is only illuminated if a threshold condition, similar to those discussed above is achieved. Some embodiments may include an additional CCD, or other known elements, to produce a video image of the area being scanned by the system 10. Display of the video image is coordinated with certain registered responses indicative of the presence of a target. These indicative responses are overlaid on the display at the pixels to which they correspond indicating the location from which the responses originate to assist in locating the target material.

In alternative embodiments, the radiation may be allowed to pass through an optical filter at one group of wavelengths, corresponding to the primary wavelengths, for capture by the CCD and storage to memory. The optical filter may then be changed or tuned to allow a second group of wavelengths, corresponding to the secondary wavelengths, to pass through for capture by the CCD and storage to memory. In additional embodiments, additional data for additional ranges of wavelengths can be further collected and stored in this way. Due to the rapidity with which the tunable optical filters may be tuned to new bandwidths, such embodiments lend themselves to the capture of relatively large numbers of data sets corresponding to different ranges of wavelengths.

The system housing can be provided as a handheld unit which can be carried by a user. Alternatively, the system housing can be a head-mount system which can include a head strap. The detector system, filter system, and optional processing modules can be housed within the head-mount system and the display provided in a wired or wirelessly connected output display which can be carried or mounted (e.g. on a belt, jacket or stationary location). In one alternative, the processor can record the data collection history as a function of time. This information can be used to correlate remotely obtained data with physical locations and/or playback by a user and a later time.

In yet another option, the system can include a haptic feedback module 38. When candidate precious or semi-precious material is detected, the haptic feedback module can be activated to notify the user of such an event. This can help to avoid missed precious or semi-precious material due to inattention or oversight. The haptic feedback module 38 can be operatively connected to the detector system 16 and/or data processor 36. The haptic response can be triggered when the reflected electromagnetic radiation has a reflected intensity corresponding to the upper reflectivity or other preset condition. Typically, the haptic response can be vibration although other responses may be useful (e.g. temperature, pressure, etc).

Reflectivity Absorption Methods

Figure 3:
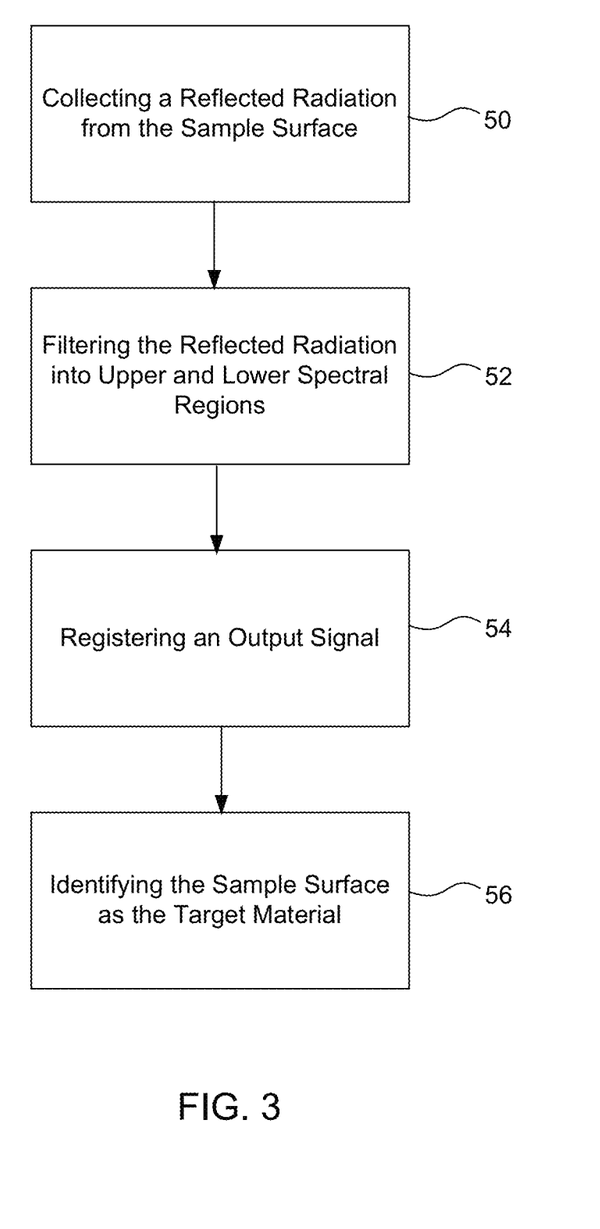
FIG. 3 is a block diagram of a method for identifying precious or semi-precious materials in accordance with one embodiment.

A method of identifying a target precious or semi-precious material can also be provided which is based on reflectivity as utilized in the above-described system. As generally illustrated in FIG. 3, the method can include collecting a reflected electromagnetic radiation from the sample surface 50. The reflected electromagnetic radiation includes a primary wavelength which corresponds to an upper reflectivity of the target material. The reflected electromagnetic radiation also includes a secondary wavelength corresponding to a lower reflectivity of the target material. Depending on the embodiment, additional ranges of wavelengths can be used to provide additional information for comparison with a standard as described more fully below. This can include detecting the radiation via a suitable detector as previously described.

The method also includes filtering the reflected electromagnetic radiation into an upper spectral region and a lower spectral region 52. Importantly, the upper spectral region encompasses the primary wavelength and excludes the secondary wavelength, while the lower spectral region encompasses the secondary wavelength and excludes the primary wavelength. Filtering for additional ranges of wavelengths may also be provided for increased confidence in comparison with a known standard. The method can further include registering a reflectivity response for the sample surface 54, with respect to one or more ranges of wavelengths. Registering can include displaying the reflectivity response in a viewable format (e.g. video, numerical, analog, etc). Alternatively, the registering can include storing reflectivity response and/or data for the reflected electromagnetic radiation. A response can be registered for both the primary wavelength and the secondary wavelength. Additional ranges of wavelengths may be registered in other embodiments in order provide additional data for processing comparisons with the stored standard.

Once the step of registering is accomplished, the method further includes identifying a candidate material as the target material 56. Identifying may comprise comparing the reflectivity response with a standard. Identifying may also comprise comparing the corresponding responses for the primary wavelength and the secondary wavelength. This identification step can be done by a user or via a computational device (e.g. a processor). The standard for comparison can be a visual brightness, flashing of the image, and/or a statistically significant data response in reflectivity and/or the response profile. Thus, in some cases, the standard can be a stored value for the target material and the identification is made by a processor.

As mentioned, the method can be applied to a variety of exploratory and/or assay scenarios. These methods are capable of locating surface exposed precious or semi-precious materials, or such materials which are visible through a medium which is transparent to the incident radiation. Typically, water is transparent to most infrared wavelengths and can be used up to several inches or several feet if the emitter and detector combination has sufficient power and resolution.

In another aspect, the sample surface can be an excavated mine wall. In this application, the method can allow for substantially real-time determination of the presence of precious or semi-precious materials in exposed rock. Further, the method can be performed along an exposed geological feature. Non-limiting examples of geological features can include riverbeds, cliff faces, outcrops, mine surfaces, and the like. In certain embodiments, these systems and methods may be deployed within a bore hole being drilled to search for precious and semi-precious materials. In other embodiments, these systems and method may be applied over a conveyor belt on which excavated materials are conveyed. In such cases, as suitable housing can be provided to allow the device to be deployed downhole or oriented adjacent excavated materials.

In yet another aspect, a mining equipment operator can be associated with the system to notify of potential locations of target materials. For example, a haptic or visual device can be triggered when target material is detected so that more careful inspection can be made before proceeding with excavation. Also, the sample surface can be tailings or other material removed from excavation operations. Regardless, the methods and system can be highly useful in providing results for materials when in their native location and without need for transport to a remote location (e.g. mine surface, assay lab, etc.).

In some embodiments, the sample surface can be illuminated via incident radiation at a single wavelength or multiple wavelengths to enhance reflection. For example, the illumination and corresponding reflectivity response can be a two frequency response or can include at least three frequencies. Additional frequencies can provide additional reference points to compare with a known or stored standard which is representative of the target material. This can increase accuracy and sensitivity of the method. The incident radiation can be provided via sunlight or other broadband light source. In this case, the step of registering can include matching the reflectivity response to a broadband reflectivity curve of the target material.

The multiple frequency reflectivity can be a broadband spectrum collected over numerous or continuous frequencies. For example, a selected band of frequencies can be chosen where spectral reflectivity responses for the target material are numerically distinguishable from other materials. Although other configurations can be used, a suitable system can include multiple sensors which are selectively filtered across the spectrum to create a corresponding reflectivity correlation curve across the spectrum. In the case of gold such a selected band can have a lower bound from about 200 nm to about 480 nm and an upper bound from about 510 nm to about 1 μm. Similarly, a selected band for silver can have a lower bound from about 200 nm to about 320 nm and an upper bound from about 400 nm to about 1 μm. Silver also has a distinct dip at about 350 nm which can be targeted as a marker to distinguish silver from surrounding materials.

Further, several frequencies can be chosen and reflectivities compared to the stored values for the target material. An optionally adjustable tolerance can be set to allow for sensitivity adjustments to compensate for non-ideal conditions (i.e. partially obscured materials, interfering materials, etc). Further, by combining reflectivity measurements over discrete spatial regions, an approximation of target material content can be calculated. This can be accomplished by an additional processing module or element which selects high density regions of the reflectivity response and calculates the surface percentage of reflectivity which matches the precious or semi-precious material. Methods such as edge detection algorithms (e.g. Gaussian and Laplace edge detection), finite element analysis, and the like can be used to identify sample regions. Alternatively, the images can be pixilated and regions analyzed by a straight count of high reflectivity pixels (i.e. statistically high intensity) versus lower intensity pixels.

Although gold and silver are exemplified throughout, other precious and semi-precious metals can also be similarly identified. Specifically, other precious metals can include platinum group elements such as platinum, palladium, ruthenium, rhodium, osmium, and iridium. In one aspect, the target precious metal can be palladium or platinum. Other semi-precious metals can include copper, lead, zinc, and alloys thereof. Further, precious materials such as gemstones (e.g. diamonds, emeralds, sapphire, and the like) can also be detected by their respective unique reflectivity patterns or values at various wavelengths. These materials also exhibit substantial variation which can be detected, especially using multi-wavelength illumination. Reflectivity data for these precious metals is shown in FIG. 2B. For example, platinum varies from about 40% reflectivity at 300 nm to about 73% at 1 μm. Similarly, palladium varies from about 54% at 450 nm up to about 81% at 2 μm. Thus, the response data can be quantitatively compared with stored values for each metal at specific frequencies.

Further, the intensity of the incident radiation can be varied with time such as in an oscillating pattern. When multiple frequencies are oscillated or varied with time, the incident radiation can also be interleaved so as to provide substantially constant illumination.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A reflectivity absorption system for identifying a target material, comprising:
   a) a detector system capable of detecting a reflected electromagnetic radiation at a primary wavelength and a secondary wavelength, said reflected electromagnetic radiation deriving from reflection of electromagnetic radiation from a sample surface, said primary wavelength corresponding to an upper reflectivity of the target material and said secondary wavelength corresponding to a lower reflectivity of the target material;
   b) a filter system operatively connected to the detector and configured to filter the reflected electromagnetic radiation into an upper spectral region and a lower spectral region, said upper spectral region encompassing the primary wavelength and excluding the secondary wavelength, and said lower spectral region encompassing the secondary wavelength and excluding the primary wavelength; and
   c) an output display configured to register an output signal in a viewable format, said output signal formed using the upper and lower spectral regions.

2. The system of claim 1, wherein the detector system is a CCD.

3. The system of claim 2, further comprising a filter layer comprising individual filters above individual sensor elements within the CCD, the individual filters distinguishable by corresponding distinct wavelengths which pass through the individual filters.

4. The system of claim 3, wherein the individual filters are arranged adjacent to one another to form a pattern comprising at least one instance of a filter tuned for every range of wavelengths that the individual filters can pass, wherein the pattern is repeated across the CCD.

5. The system of claim 1, wherein the filter system comprises at least one tunable optical filter, the tunable optical filter configured to collect data for multiple ranges of wavelengths relevant to reflection responses characteristic of the target material.

6. The system of claim 1, wherein the primary wavelength and the secondary wavelength are selected from infrared, ultraviolet, and visible.

7. The system of claim 1, wherein the primary wavelength is from about 650 nm to about 1 μm.

8. The system of claim 1, wherein the upper reflectivity is greater than 95%.

9. The system of claim 1, wherein the lower reflectivity of the target material is at least 20% lower than the upper reflectivity.

10. The system of claim 1, wherein the target material is selected from the group consisting of gold, silver, platinum, palladium, ruthenium, rhodium, osmium, iridium, copper, lead, zinc, alloys thereof, diamonds, emeralds, sapphire, and combinations thereof.

11. The system of claim 1, wherein the target material is gold.

12. The system of claim 1, wherein the target material is a precious material.

13. The system of claim 1, wherein the filter system is oriented to filter the reflected electromagnetic radiation prior to detection by the detector system.

14. The system of claim 13, wherein the filter system includes a first band-pass filter to form the lower spectral region and a second band-pass filter to form the upper spectral region.

15. The system of claim 13, wherein the filter system includes a low-pass filter to form the upper spectral region and a high-pass filter to form the lower spectral region.

16. The system of claim 1, wherein at least one additional range of wavelengths is filtered and detected for use in forming the output display.

17. The system of claim 1, further comprising a data processor configured to transform the upper spectral region and the lower spectral region into the output signal.

18. The system of claim 1, wherein the output signal is a video image.

19. The system of claim 1, further comprising a haptic feedback operatively connected to the detector system and configured to provide a haptic response when the reflected electromagnetic radiation has a reflected intensity corresponding to the upper reflectivity and the lower reflectivity.

20. A method of identifying a target material, comprising:
   a) collecting a reflected electromagnetic radiation from a sample surface, said reflected electromagnetic radiation including a primary wavelength corresponding to an upper reflectivity of the target material and a secondary wavelength corresponding to a lower reflectivity of the target material;
   b) filtering the reflected electromagnetic radiation into an upper spectral region and a lower spectral region, said upper spectral region encompassing the primary wavelength and excluding the secondary wavelength, and said lower spectral region encompassing the secondary wavelength and excluding the primary wavelength;
   c) registering an output signal formed using the upper and lower spectral regions; and
   d) identifying the sample surface as the target material by comparing the reflectivity response with a standard.

21. The method of claim 20, wherein the reflected electromagnetic radiation is produced from sunlight.

22. The method of claim 20, wherein the registering includes matching the upper and lower spectral regions to a broadband reflectivity curve of the target material.

23. The method of claim 20, wherein the filtering includes time sequenced oscillation to form a flickering output signal from the upper and lower spectral regions such that visible flicker in the output signal corresponds to substantial changes in reflectivity of the sample surface between the upper spectral region and the lower spectral region.

24. The method of claim 20, wherein the standard is a stored value for the target material, and the identifying is performed by a data processor.

* * * * *